(12) United States Patent
Akpan (10) Patent No.: US 8,924,023 B2
(45) Date of Patent: Dec. 30, 2014

(54) EVALUATING DOSING FROM AN IMPLANTABLE INFUSION DEVICE

(75) Inventor: Emem Akpan, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 299 days.

(21) Appl. No.: 13/085,621

(22) Filed: Apr. 13, 2011

(65) Prior Publication Data

US 2012/0265033 A1    Oct. 18, 2012

(51) Int. Cl.
*A61B 5/00* (2006.01)
*A61M 5/172* (2006.01)

(52) U.S. Cl.
CPC ............ *A61B 5/4839* (2013.01); *A61M 5/1723* (2013.01); *A61B 2560/0276* (2013.01); *Y10S 128/92* (2013.01); *Y10S 128/923* (2013.01)
USPC .......... 700/266; 702/19; 600/373; 604/890.1; 604/891.1; 604/892.1; 604/19; 604/131; 604/288.01; 604/288.02; 604/288.03; 604/288.04; 604/502; 604/93.01; 604/175; 606/248; 607/59; 607/60; 128/920; 128/923

(58) Field of Classification Search
CPC .................... A61M 5/1723; A61B 2560/0276; A61B 5/4839
USPC .......... 700/266; 702/19; 600/373; 604/890.1, 604/891.1, 892.1, 19, 131, 288.01–288.04, 604/502, 93.01, 175; 606/248; 607/59, 60; 128/920, 923

See application file for complete search history.

(56) References Cited

U.S. PATENT DOCUMENTS

| 5,006,997 | A | 4/1991 | Reich |
| 5,328,460 | A | 7/1994 | Lord |
| 7,096,067 | B2 | 8/2006 | Linberg |
| 2002/0095196 | A1 * | 7/2002 | Linberg ........................ 607/60 |
| 2002/0148477 | A1 * | 10/2002 | Kwoen ........................ 128/920 |
| 2010/0222846 | A1 | 9/2010 | Goetz |

FOREIGN PATENT DOCUMENTS

| WO | WO 2007/123764 | 11/2007 |
| WO | WO 2008/121581 | 10/2008 |

* cited by examiner

*Primary Examiner* — Shogo Sasaki
(74) *Attorney, Agent, or Firm* — Mueting, Raasch & Gebhardt P.A.

(57) ABSTRACT

A method for evaluating dosing from an implanted infusion system that includes receiving input regarding the identity of a therapeutic agent into an external device. The method further includes displaying on the external device a predetermined set of symptoms associated with the therapeutic agent; receiving input into the external device regarding with which of the symptoms the patient presents; and determining whether the therapeutic agent is being delivered, or has been delivered, at an appropriate dose based on the input identity of the therapeutic agent and the input symptoms.

13 Claims, 11 Drawing Sheets

Therarpeutic Agent A

- Pale Skin
- Easy Bruising or Bleeding
- Unusual Weakness
- Mouth Sores
- Nausea
- Vomiting
- Black or Bloody Stool
- Coughing Up Blood
- Infrequent Urination

---

- Headaches
- Dizziness
- Tiredness
- Blurred Vision
- Loss of Balance

OVERDOSE

| Possible Causes | Probability of Occurrence |
|---|---|
| Programming Error | 95% |
| Incorrect Drug/Concentration | 35% |
| Battery Depletion | 5% |
| Pump Motor Stall | 5% |
| Catheter Tear or Break | 50% |
| Catheter Dislodgement | 60% |
| Catheter Occlusion | 30% |

EVALUATING DOSING FROM AN IMPLANTABLE INFUSION DEVICE

FIELD

The present disclosure relates generally to systems and methods for identifying whether an implantable therapy delivery system is delivering an appropriate dose of therapeutic agent and for identifying potential sources of inappropriate dosing.

BACKGROUND

Implantable infusions systems have been used to treat a variety of diseases, such as spasticity, pain and cancer by targeting drug delivery to a selected area of a patient. Therapies employing such systems have proven to be very helpful for patients for which systemic therapy is not effective, possible, or practicable. The implantable systems typically include an implantable infusion device containing a reservoir for housing the drug and a catheter coupled to the reservoir to direct the drug to the target area. The devices typically include a pump or mechanism for driving fluid from the reservoir, or withdrawing fluid from the reservoir, and through the catheter.

Most implantable infusion devices closely control the rate at which the drug is delivered to ensure that the patient receives an appropriate dose of the drug. However, there may be instances in which inappropriate dosing (e.g., under-dose or overdose) occurs. Many current devices have electronics or sensors that allow for monitoring of malfunctions, such as battery depletion or stalling of the pump. Some infusion devices have been proposed that are capable of monitoring catheter complications, such as a leak, a dislodgement, or an occlusion. Upon detection of an infusion device or catheter malfunction or the likelihood of such a malfunction, the device may alert the patient to seek medical attention. The malfunction event may be stored in device memory and may be retrieved by a healthcare provider upon a patient visit so that the nature of the malfunction can be ascertained by the healthcare provider.

However, infusion device or catheter malfunctions are not the only source of inappropriate dosing. In some instances, the infusion device may be programmed or set to deliver the drug at a rate that is too high or too low for the therapy that the patient is receiving; a particular patient may not respond, or may be too sensitive, to a given drug relative to the general population; the concentration of the drug introduced into the reservoir may be higher or lower than intended or appropriate; etc. In such cases, the infusion device and catheter may be perfectly functional, but the patient does not receive a dose of the drug that is appropriate for the therapy. In these cases, it can be difficult to identify the source of the inappropriate dose or even that an inappropriate dose has been, or is being, delivered.

For example, a healthcare provider may interrogate the infusion device to determine the drug infusion parameters. However, if the healthcare provider is the one who set the parameters initially, the parameters may appear perfectly appropriate. In addition, it may not be readily apparent in all cases which of the patient's symptoms are indicative of an under- or overdosing of the drug.

SUMMARY

This disclosure, among other things, describes devices, systems and methods for determining whether a patient is receiving an appropriate dose of a therapeutic agent from an implantable infusion system. The systems, devices and methods take into account patient symptoms. In particular, a healthcare provider is presented with a predetermined set of symptoms known or suspected to be associated with the drug delivered to the patient via the implantable infusion system and selects the symptoms with which the patient presents. The devices, systems and methods described herein utilize input regarding the selected symptoms to determine whether the patient is receiving the appropriate dose, an under-dose, or an overdose of the therapeutic agent. By taking into account the patient's symptoms, the methods, systems, and devices described herein allow for improved detection of inappropriate dosing via an implantable infusion system. A list of symptoms that are indicative of inappropriate dosing or side effects that are tailored to a particular therapeutic agent (e.g., baclofen, morphine, or methotrexate) in a particular patient population (e.g., patients having an implantable infusion device) receiving a particular therapy (e.g. administration via spinal intrathecal space) allows for better diagnosis of inappropriate dosing.

If the patient's symptoms are indicative of an inappropriate dose (e.g., under- or overdose), further investigation of the potential sources of the inappropriate dosing may be investigated. For example, the infusion device may be interrogated to determine whether an infusion device or catheter malfunction or complication has occurred.

In various embodiments, a method for gauging the performance of an infusion system implanted in a patient is described herein. The infusion system includes an infusion device having a reservoir for containing the therapeutic agent and a catheter operably coupled to the reservoir for delivering the therapeutic agent to a predetermined location of the patient. The method includes receiving input regarding the identity of the therapeutic agent into an external device. The external device is capable of communicating with the implanted infusion device. The method further includes displaying on the external device a predetermined set of symptoms associated with the therapeutic agent. The method also includes receiving input into the external device regarding with which of the symptoms the patient presents and determining whether the therapeutic agent is being delivered, or has been delivered, at an appropriate dose based on the input identity of the therapeutic agent and the input symptoms. The method may additionally include displaying on the external device whether the patient is receiving the appropriate dose of the therapeutic agent.

In some embodiments, the above-described method further includes interrogating the infusion device to identify potential sources of inappropriate dosing if it is determined that the therapeutic agent is not being delivered, or has not been delivered, at an appropriate dose. Potential sources of inappropriate dosing may be displayed on the external device based on data received as a result of the interrogation. The method may also include calculating a probability that the potential source contributes to the inappropriate dosing and displaying the probability for each of the displayed potential sources. Examples of potential sources that may be displayed include (i) programming error; (ii) incorrect therapeutic agent; (iii) incorrect concentration of therapeutic agent; (iv) battery depletion; (v) pumping mechanism failure; (vi) catheter tear or break; (vii) catheter occlusion; (viii) catheter migration; and (ix) catheter dislodgement. The method may further include calculating a probability that the potential source contributes to the inappropriate dosing and displaying the probability for each of the displayed potential sources.

The method may further include displaying potential diagnostic interventions for the displayed potential sources of inappropriate dosing and may include prompting a user to select a diagnostic intervention. In some embodiments, the infusion device is instructed to perform a catheter complication test and the potential catheter complications, such as catheter break or tear, catheter migration, catheter dislodgement, and catheter occlusion, may be displayed, as well as the probability of existence for each of the displayed catheter complications.

In various embodiments, an external device capable of communicating with an implantable infusion device is described herein. The external device includes telemetry components for wirelessly communicating with the implantable infusion device; a display for presenting information to a user; an input source for receiving input from the user; and electronics. The electronics are operably coupled to the telemetry components, the display, and the input source. The electronics are programmed with instructions that cause the external device to (i) receive input regarding the identity of a therapeutic agent being delivered from the implantable infusion device; (ii) display a list of potential patient symptoms associated with the therapeutic agent; (iii) receive input into the external device regarding from which of the potential symptoms the patient suffers; (iv) determine whether the therapeutic agent is being delivered, or has been delivered, at an appropriate dose to the patient based on the input identity of the therapeutic agent and the input symptoms; and (v) display whether the patient is receiving the appropriate dose of the therapeutic agent. In some embodiments, the instruction further cause the electronics to calculate probabilities that the potential sources contribute to the inappropriate dosing and display the probability for each of the displayed potential sources.

The electronics of the above-described external device may be configured to communicate with a remote database to aid in determining whether the therapeutic agent is being delivered, or has been delivered, at an appropriate dose to the patient based on the input identity of the therapeutic agent and the input symptoms.

One or more embodiments of the systems, devices and methods described herein may provide one or more advantages over prior systems, devices and methods for determining whether a patient is receiving, or has received, an inappropriate dose of a therapeutic agent from an implantable infusion system. By taking into account patient symptoms, determinations may be made on a patient-by-patient basis. By presenting for selection a predetermined set of symptoms that are known or suspected to be relevant to a particular therapeutic agent or therapy, diagnosis may be improved by limiting input to relevant information. The methods, devices and systems described herein may allow for the predetermined symptoms to be updated as additional information is obtained, allowing further refinement with time. In some embodiments, the information regarding the patient's symptoms is combined with information regarding device status (e.g. infusion device or catheter complication or malfunction) to facilitate identifying the potential sources of error in dosing. In some embodiments the probability that a particular potential source of error exists is presented, allowing for informed decisions to be made with regard to intervention steps to be taken. In many cases, the devices, systems and methods described herein provide guidance with regard to the steps to be taken for intervention and diagnosis of potential sources of inappropriate dosing. These and other advantages of one or more embodiments of the methods and systems described herein will be apparent to those of skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

This disclosure relates to, among other things, systems and methods for identifying whether an implantable therapy delivery system is delivering an appropriate dose of therapeutic agent and for identifying potential sources of inappropriate dosing. The systems, devices and methods take into account patient symptoms that are preselected based on the therapeutic agent being delivered to a patient or the particular therapy that the patient is receiving. The preselected symptoms are those known or suspected to be associated with the therapeutic agent or therapy. By taking into account the patient's symptoms, the methods, systems, devices, and the like described herein allow for improved detection of inappropriate dosing via an implantable infusion system. By presenting a preselected set of symptoms that are indicative of inappropriate dosing or side effects that are tailored to a particular therapeutic agent in a particular patient population receiving a particular therapy, more reliable and accurate diagnosis of inappropriate dosing may be possible.

Figure 1:
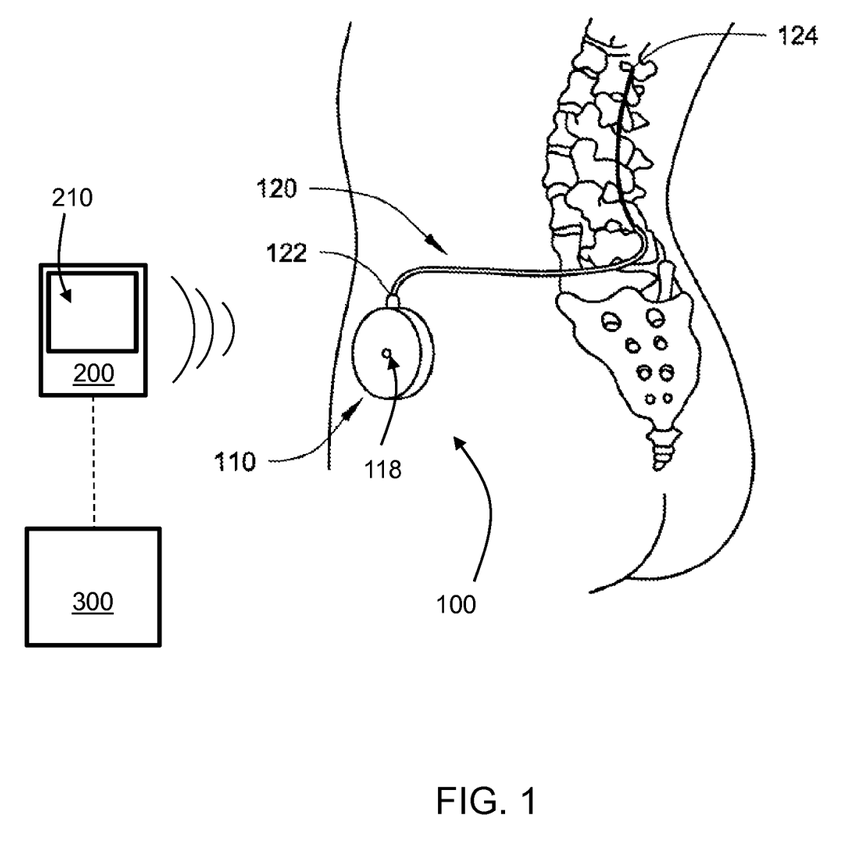
FIG. 1 is schematic view showing an infusion system implanted in a patient, along with an external device and remote database.

The devices, systems, methods and the like described herein may be employed with any suitable implantable infusion system. FIG. 1 shows an example of an infusion system 100 that may be employed in accordance with the teachings presented herein. The infusion system depicted in FIG. 1 includes an infusion device 110 and a catheter 120. The catheter 120 is operably coupled to the infusion device 110 such that the catheter 120 is in fluid communication with a reservoir (not shown in FIG. 1) of the device 110. The depicted infusion device 110 includes a refill port 118 in communication with the reservoir disposed within the housing of the device 110, which allows the supply of therapeutic agent in the reservoir to be replenished. The infusion device 110 may include any suitable mechanism or structure capable of delivering one or more fluids to a patient. The structures used to drive fluids in the infusion devices may be powered (e.g., piston pumps, diaphragm pumps, peristaltic pumps, etc.), may be activated based on pressure to drive fluid out of a reservoir (e.g., using collapsing diaphragms, expanding bladders, osmotic, etc.), or the like. The infusion device 110 may contain a catheter access port (not shown in FIG. 1) in communication with the catheter 120.

The infusion system 100 depicted in FIG. 1 is shown implanted in a patient. The proximal end 122 of the catheter 120 is coupled to the infusion device 110. The infusion device 110 may be surgically implanted in any suitable location, such as subcutaneously in the pectoral, abdominal or other region of the subject's body. The distal end 124 of the catheter 120 is implanted in a patient such that the distal end 124 is located at the selected internal delivery site in the patient (in the intrathecal space of the patient as depicted in FIG. 1, the cerebroventricles, or elsewhere as desired).

In some embodiments, the infusion system 100 does not include a separate catheter 120, but rather the infusion device 110 is implanted in the target region of the patient and the therapeutic agent is administered directly to the target region via an outlet of the infusion device.

An external device 200 capable of wireless communication with the implanted infusion device 110 is also shown in FIG. 1. The depicted external device 200 includes a display 210 for presenting information to a user, such as a healthcare provider. The external device 210 is capable of receiving input regarding the patient's symptoms, the identity of the therapeutic agent, and the like. The display 210 may present a graphical user interface that allows a user to select or enter patient symptoms, may present information regarding whether the patient is receiving an appropriate dose of therapeutic agent, may provide guidance regarding intervention or diagnostic steps taken or to be taken, or the like; e.g. as discussed in more detail below.

Also depicted in FIG. 1 is a remote database 300 with which the external device 200 may communicate. The database 300 may include information regarding symptoms from a population of patients receiving a particular therapy; e.g., intrathecal baclofen for treatment of spasticity. The database 300 may also include information regarding infusion system parameters and status that may be used in conjunction with patient symptoms to identify potential sources of dosing issues. For example, the database 300 may include information regarding drug concentration, delivery rate, delivery location, disease being treated, appropriate dosing ranges, symptoms of patients that have been attributed to underdosing, symptoms of patients that have been attributed to overdosing, symptoms of patients that have been attributed to side effects, infusion device performance parameters or status, catheter performance parameters or status, or the like. The database 300 may include information regarding any number of patients and may be updated from time to time. In some embodiments, the remote database 300 is updated following presentation of new information from the external device 200. The remote database 300 may be housed in memory of an appropriate device, such as a server or other computer, programmer (such as a physician programmer), or the like.

The external device 200 may compare input data regarding patient symptoms or system parameters or status to data in the database 300 to determine whether the patient is receiving an appropriate dose of therapeutic agent or the potential sources for an inappropriate dose. In some embodiments, the database 300 is associated with a processor programmed with instructions that allow the database processor to make such determinations and to provide information regarding the determinations to the external device 200. In some embodiments, no remote database 300 is employed and relevant data is stored in the external device 200; e.g., in a lookup table.

Any suitable external device, such as a programmer (e.g., a Medtronic, Inc. N'Vision® clinician programmer or a Medtronic, Inc. myPTM® patient programmer), a tablet computer, a smart phone, a personal data assistance, a laptop computer, or the like, may be employed. In some embodiments, the external device 200 is a desktop computer with an associated monitor serving as the display 210.

Figure 2:
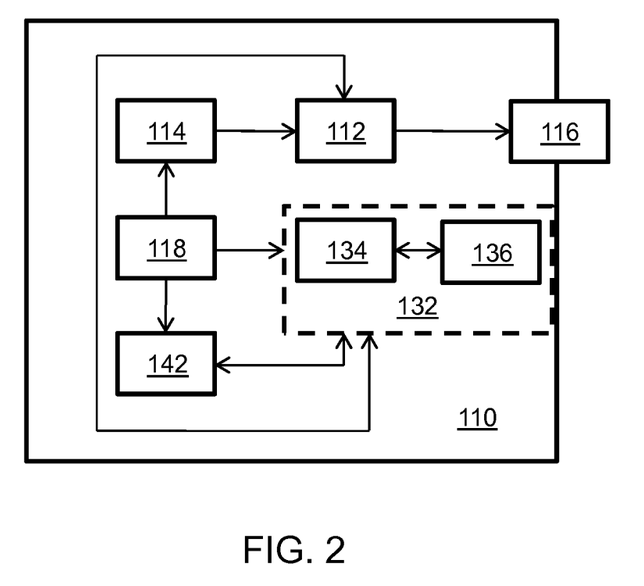
FIG. 2 is a schematic block diagram showing some selected components of an implantable infusion device.

Referring now to FIG. 2, some selected components that an infusion device 110, an external device 200 and a remote device 360, in which the database 300 is stored, may include are depicted in block form. The infusion device depicted in FIG. 2 includes infusion rate control components 112, such as a pump, valves, or the like, operably coupled to a reservoir 114. The infusion rate control components 112 control the rate at which fluid from the reservoir 114 exits outlet 116, to which a catheter may be coupled. While shown as upstream of the reservoir 114, the infusion rate control components 112 may be upstream or downstream, or some components upstream and some downstream, of the reservoir 114, depending on the particular configuration of the infusion device 110 employed.

The depicted infusion device 110 also includes a power supply 118 operably coupled to the pumping mechanism 112, to control electronics 132, and to telemetry components 142.

Telemetry components 142 may include, for example, a telemetry antenna, an analog to digital convertor, or the like. The telemetry components 142 are in communication with the control electronics 132 which can translate or encode or decode information sent or received through the telemetry antenna. The control electronics 132 are also operably coupled to the infusion rate control components 112 to control the rate of infusion of a therapeutic agent from the reservoir based on programmed instructions. The control electronics 132 may include a processor 134 and memory 136 as shown, as well as any other suitable or necessary components. Memory 136 may be RAM, ROM or the like. In many embodiments, memory 136 includes RAM and ROM. Instructions with regard to infusion rate or device status may be stored in memory. Typically, following implantation of the device 110 or on refill of the reservoir 114, instructions or data regarding the infusion rate, the disease treated, and the concentration of therapeutic agent introduced into the reservoir are transmitted to the device 110 and stored in memory 136.

Figure 3:
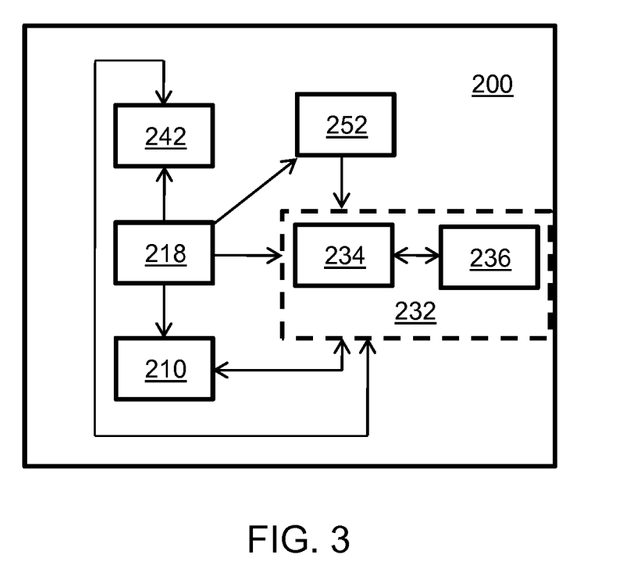
FIG. 3 is a schematic block diagram showing some selected components of an external device capable of communicating with an implanted infusion device.

Referring now to FIG. 3, a schematic block diagram of some selected components of an external device 200 capable of communicating with an implanted infusion device is shown. The external device 200 includes a power supply 218 operably coupled to telemetry components 242, display 210, and control electronics 232. The telemetry components 242 are configured to allow communication with the implanted infusion device and may allow for communication with a remote database. Alternatively, other communication components (not shown) may be employed to communicate with the remote database.

The telemetry components 242 are in communication with the control electronics 232 which can translate or encode or decode information sent or received through the telemetry components, such as a telemetry antenna. The control electronics 232 are also operably coupled to the display 210. In some embodiments, the display 210 may serve as an input; e.g., the display may be a touch-screen display. Alternatively or in addition, the device 200 may have a separate input source 252, such as a keyboard or keypad, which may be coupled to power supply 218. The control electronics 232 may include one or more processors 234 and memory 236 operably coupled to the one or more processors 234. Information regarding patient symptoms may be stored in memory 236, e.g., in the form of a lookup table. Processor 234 may compare input patient symptoms or device performance or status information to information stored in memory 236 in determining whether the patient is receiving an appropriate dose of therapeutic agent from the implanted infusion system.

Figure 4:
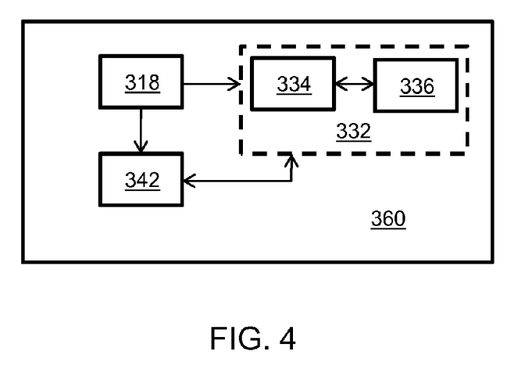
FIG. 4 is a schematic block diagram showing some selected components of a remote database.

Referring now to FIG. 4, a remote device 360, in which a database may be stored, is shown in schematic block form. The remote device 360 includes a power supply 318 operably coupled to communication components 342 and to control electronics 332. The communication components 342 are configured to allow communication between the remote device 360 and an external device (e.g., external device 200 of FIG. 3) and possibly other similar devices. Such communications may be via the internet, direct or wired connection, wireless communication, or the like. The control electronics 332 includes a processor 334 and memory 336. Information regarding patient symptoms for various therapeutic agents delivered at various doses to various different locations may be stored in memory. Such information may include ranges of doses considered appropriate or too high or too low. Additional information regarding particular infusion device performance and status may also be stored in memory 336. Further, determinations as to whether a particular set of parameters or ranges of parameters with regard to symptoms, dosing, or infusion system performance are indicative of appropriate or inappropriate dosing may be stored in memory 336. In addition, potential sources of inappropriate dosing based on symptoms, dosing, and infusion system performance parameters may be stored in memory 336. The data regarding symptoms, dosing, or infusion system parameters may be updated from time to time; e.g. as additional patient information becomes available, and may be stored in memory 336, e.g. in a lookup table. Such data may be stored in the memory of the external device rather than, or in addition to, storing such information in the memory of the remote device 360.

Processor 334 of remote device 360 may be used to determine whether a patient's symptoms are indicative of an overdose, and under-dose, a side effect or the like; to identify potential sources of inappropriate dosing; to calculate a probability that a potential source contributes to inappropriate dosing; or the like. For example, processor 334 may receive relevant data from an external device via communication components 342 and may compare the received data to data stored in memory 336 in making desired determinations or calculations. Data regarding the outcomes of the determinations or calculations may then be transmitted to the external device (e.g., device 200 in FIG. 1 or 3) via communication components 342. The external device may then display the results or a summary of the results on its display or monitor. In some embodiments, some or all of these determinations or calculations are made by a processor (e.g., processor 234) of external device (e.g., device 200).

Figure 5:
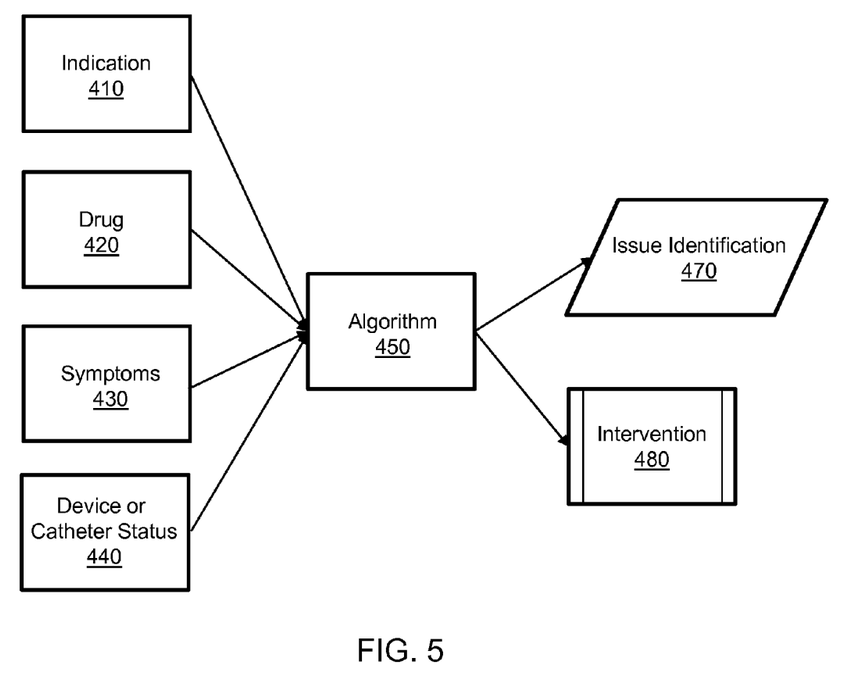
FIG. 5 is a schematic high level view of data processing that may occur with regard to some embodiments described herein.

Referring now to FIG. 5, a high level scheme of data processing according to various embodiments is shown. As shown in FIG. 5, an algorithm 450 receives input 410, 420, 430, 440 and produces output 470, 480. The input may include (i) the therapy indication 410; e.g., the disease treated, the location of delivery (e.g., lumbar intrathecal space), the make and model of infusion device employed, the infusion parameters, or the like; (ii) the therapeutic agent or drug being delivered 420, which can include data regarding the concentration and infusion rate; (iii) the symptoms of the patient 430; (iv) infusion device or catheter status or complications 440; or (v) the like. The algorithm 450 may process the input 410, 420, 430, 440, which may include comparing input data to data stored in a lookup table, to produce output 470, 480. The output may include identifying potential issues 470, such as reporting whether an inappropriate dose of the therapeutic agent is, or has been delivered, identifying potential sources of inappropriate dosing, or reporting the probability that a particular potential source contributes, or has contributed, to the inappropriate dosing. The output may additionally, or alternatively, include reporting potential diagnostic or intervention processes 480 that may be taken. More details regarding the algorithmic or methods steps that may be employed in accordance with various embodiments are described below with reference to FIGS. 6 and 8-11.

Figure 6:
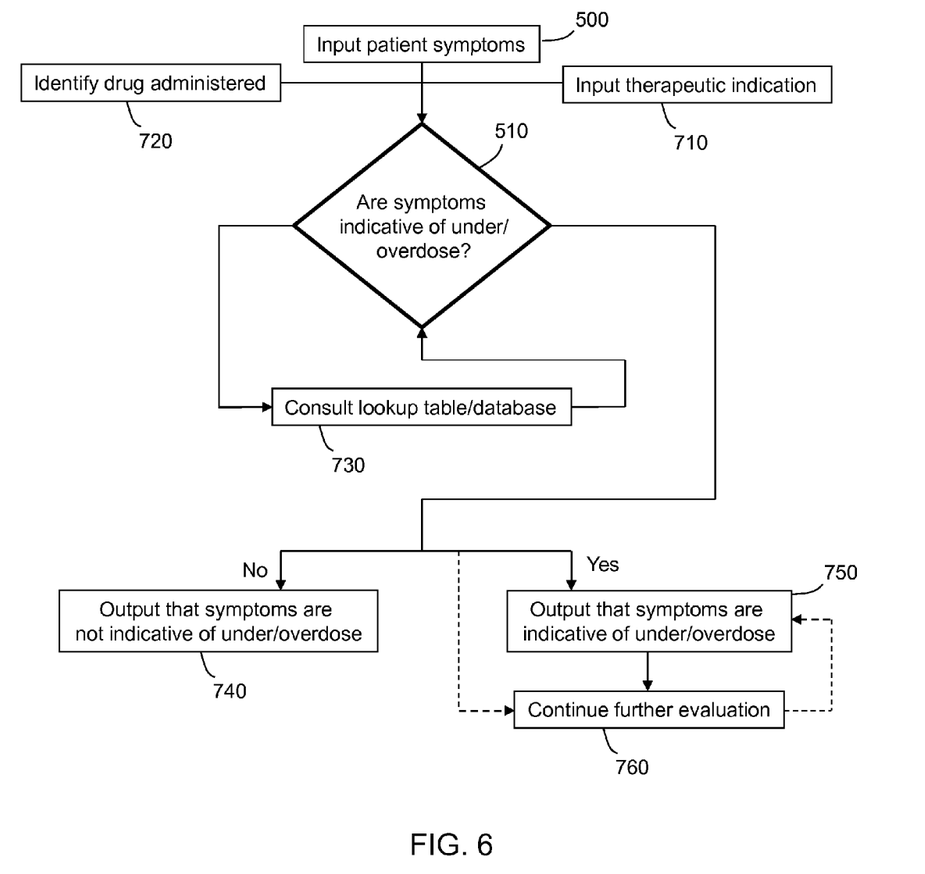
FIG. 6 is a flow diagram showing a method or algorithm in accordance with various embodiments described herein.

Referring now to FIG. 6, a method for determining whether patient symptoms are indicative of inappropriate dosing is shown. In the depicted methods, data regarding the therapeutic agent being administered is input (720). Such data may include one or more of the identity of the therapeutic agent, the concentration of the therapeutic agent being delivered, the rate of delivery, dosing information, and the like. The information regarding the therapeutic information may be obtained from the implanted infusion device, as such information is typically stored in memory of the implanted infusion device at implantation or refill. The information may be input into an external device for further processing.

Figure 7:
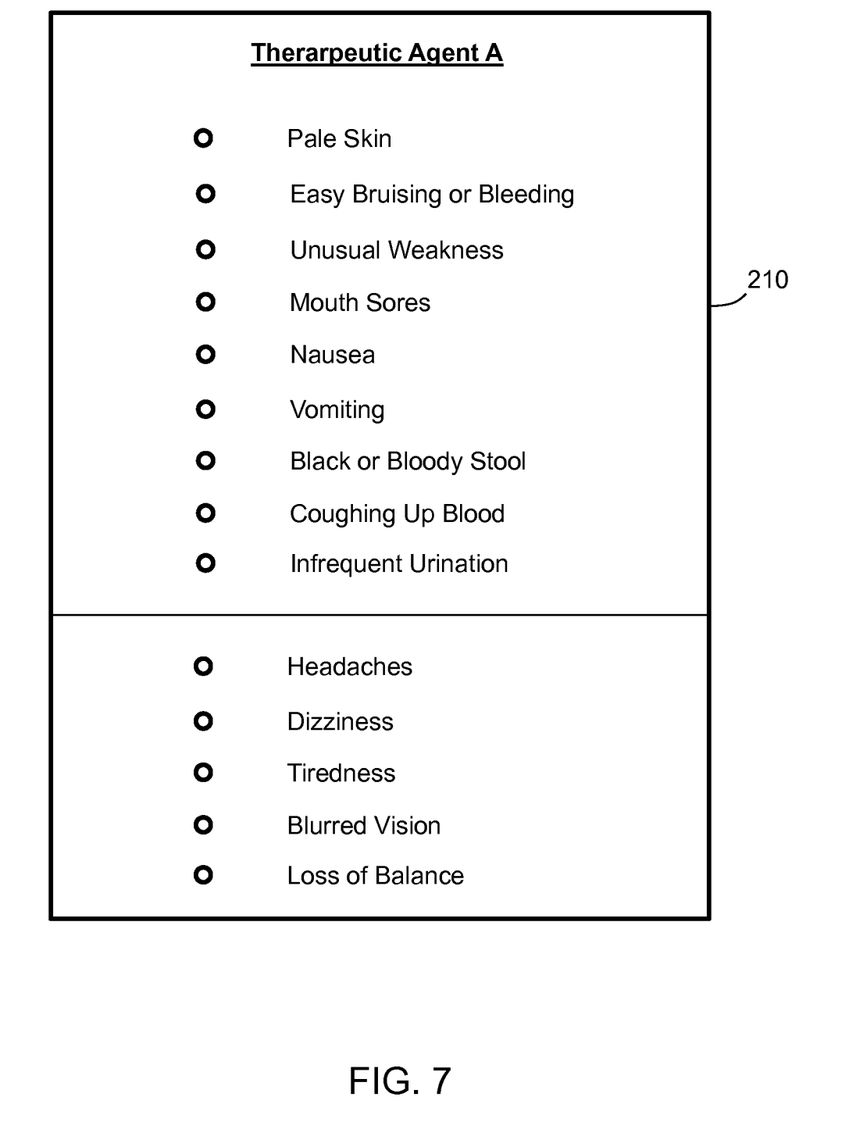
FIG. 7 is a schematic screenshot of an example of a display that may be presented in accordance with an embodiment described herein.

In the embodiment depicted in FIG. 6, data regarding patient symptoms is also input (500). Preferably, the input patient symptoms are related to, or indicative of, the therapeutic agent being administered. In some embodiments, the patient symptoms to be input are presented to a user and are preselected as being relevant or indicative of the therapeutic agent being administered. The user may then select with which of the symptoms the patient presents. For example and with reference to FIG. 7, a list of indicative symptoms may be presented on a display 210, such as a display of an external device 200 as depicted in FIG. 1. In the example depicted in FIG. 7, the symptoms presented are examples of symptoms that may commonly occur with a therapeutic agent. The symptoms above the horizontal line are symptoms commonly associated with overdoses of "therapeutic agent A" and symptoms presented below the horizontal line are symptoms associated with side effects of therapeutic agent A. Of course, the preselected symptoms may be presented in any suitable manner other than a list as shown in FIG. 7.

It will be understood that similar preselected symptoms may be presented for other therapeutic agents that are delivered. It will be further understood that the preselected symptoms may be indicative of situations other than overdosing and side effects. For example, the symptoms associated with a particular therapeutic agent may be indicative of underdosing, abrupt withdrawal, varying degrees of overdosing, underdosing or the like, or the like.

By presenting preselected symptoms known to be associated with a given therapeutic agent, the ability to determine whether the patient is receiving an appropriate dose of the therapeutic agent is increased relative to imputing symptoms that may not relate to the agent. It will be understood that the preselected symptoms may be updated from time to time as additional information is obtained with regard to symptoms associated with a therapeutic agent.

A determination as to whether an input symptom or set of symptoms is indicative of inappropriate dosing may be made, in whole or in part, by reference to a lookup table. In some embodiments, particular symptoms may be weighted according to their predictive value. For example, mouth sores and coughing up blood may be more highly predictive of a therapeutic agent A overdose than pale skin. Such factors may be taken into account in determining whether a patient is receiving an appropriate dose of a therapeutic agent from an implanted infusion device.

Referring again to FIG. 6, data regarding therapeutic indication may be input (710). This data may include information regarding the target location of delivery, the disease being treated, and the like. It will be understood that the symptoms with which a patient presents will depend in part on such factors. The information presented in a lookup table or algorithm may take into account such factors.

Taking into account one or more of input data regarding the administered therapeutic agent (720), the therapeutic indication (710), and patient symptoms (500), a determination may be made as to whether the symptoms are indicative of inappropriate dosing (510). Such a determination may be made by an external device (e.g. device 200 as depicted and described above or remote database 300 as depicted and described above). The determinations may be made in whole, or in part, through the use of a lookup table (730).

It may be desirable to present output (e.g. via display 210 as depicted and described above) that the symptoms are not indicative of inappropriate dosing (740) if it is so determined (510). If the symptoms are indicative of inappropriate dosing, output to that effect (750) may be desired. It may also be desirable to continue with further evaluation (760), such as evaluation of device or catheter status as discussed above. Such further evaluation (760) may be desirable before or after output is presented that the symptoms are indicative of inappropriate dosing (750).

Figure 8:
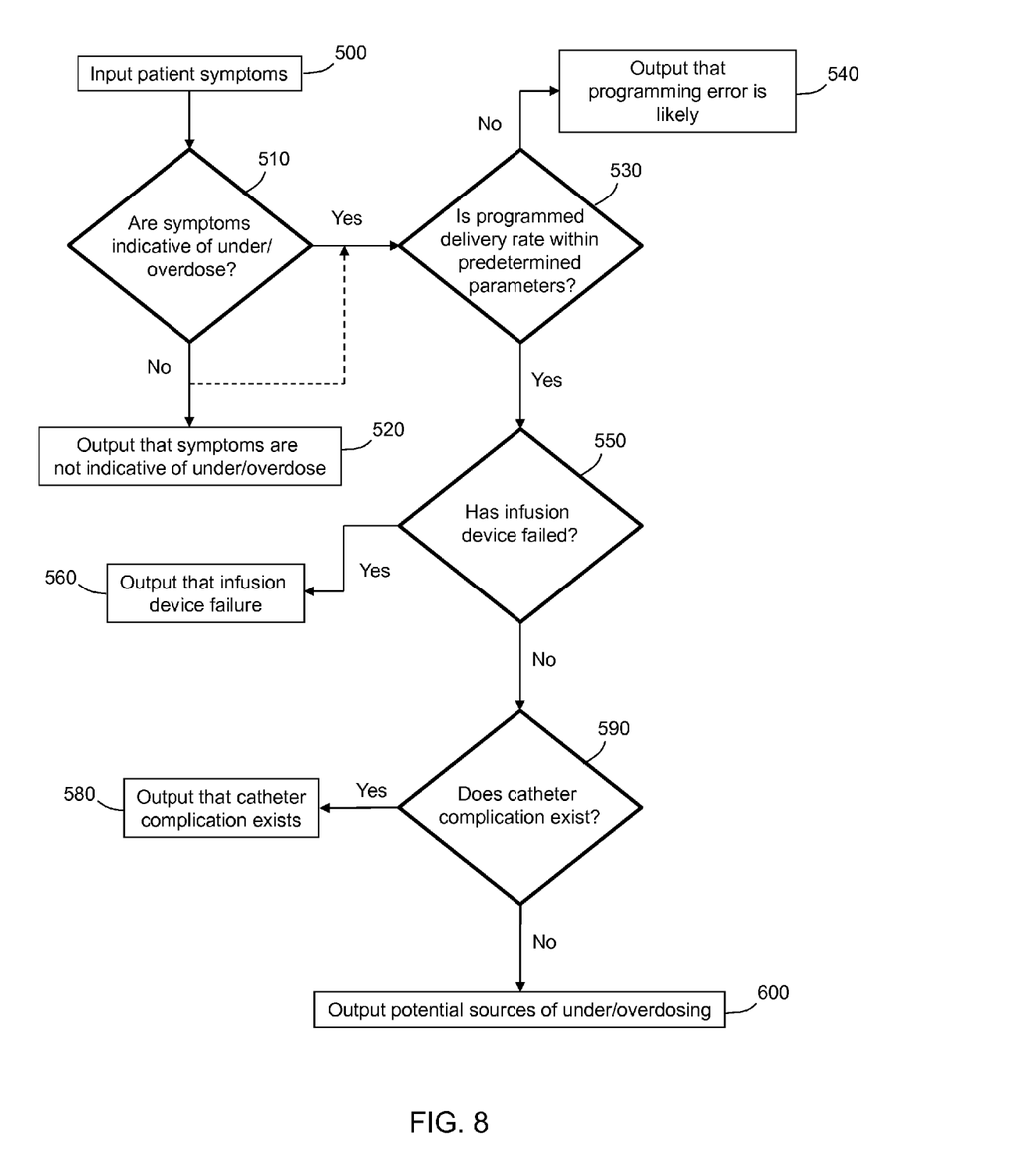
FIGS. 8-11 are flow diagrams showing methods or algorithms in accordance with various embodiments described herein.

Referring to FIG. 8, an embodiment of a method or algorithm is shown. The method includes inputting patient symptoms (500), e.g. into an external device, and determining whether the symptoms are indicative of an inappropriate dose (e.g., under- or overdose) (510). Of course, information regarding the therapeutic agent and the therapy may also be input and used in the determination. If the symptoms are determined not to be indicative of an inappropriate dose, output may be presented to that effect (520), e.g., via a display of an external device. In addition and as shown in FIG. 8, it may be desirable to sequentially determine (i) whether the delivery parameters programmed in the infusion device are within acceptable predetermined parameters (530), (ii) whether the infusion device has failed (550), e.g., whether a battery has been depleted or a pumping mechanism has failed, and (iii) whether a catheter complication exists (590).

By way of example, an external device (e.g., device 200 as depicted and described above) capable of communicating with the implanted infusion device may interrogate the infusion device to receive data regarding delivery the therapeutic agent being delivered, the programmed delivery parameters, and the status of the device or components. The external device (or remote device in communication with the external device) may use the data provided by the infusion device to make appropriate determinations and may output or display whether a programming error is a likely source of inappropriate dosing (540), whether a device failure, such as a depleted battery or stalled pump, is a likely source of inappropriate dosing (550), or whether a catheter complication may be a likely source of inappropriate dosing (580). If determinations as to whether the programmed delivery parameters (530), failure of the infusion device (550), and catheter complication (590) are inconclusive, output to this effect may be presented. In addition or alternatively, a list of potential sources (even though inconclusive) may be presented (600).

In some embodiments, a determination as to the probability that a particular source of inappropriate dosing contributes to the inappropriate dosing may be made and output to this effect may be presented. This may be particularly helpful to a user where no conclusive device or catheter complication has been determined to exist (600).

Figure 9:
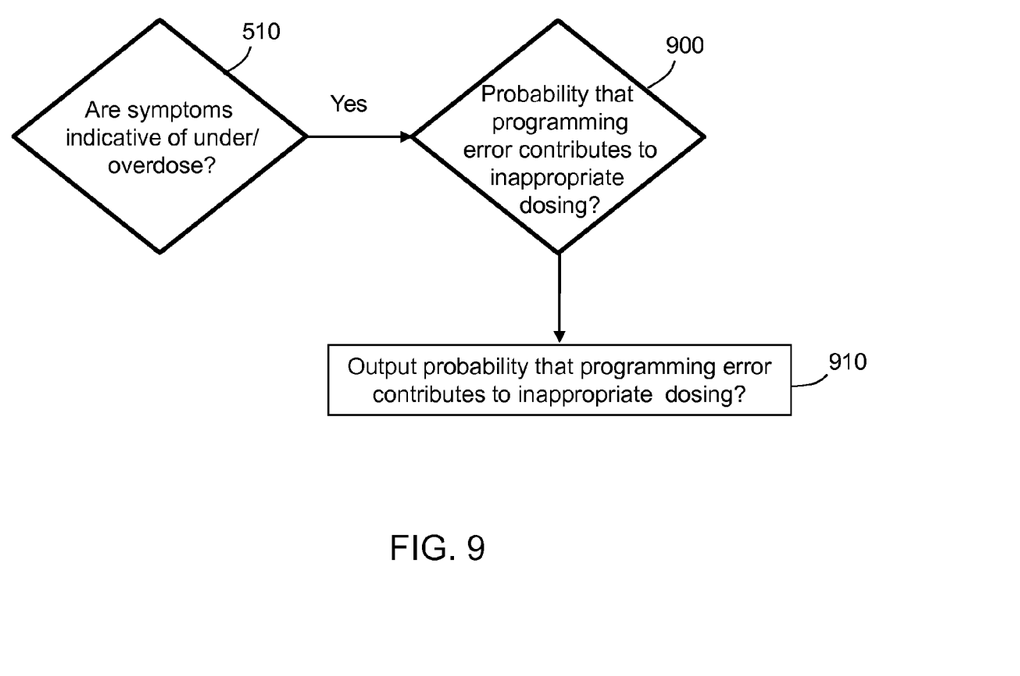

Referring now to FIG. 9, an example of a method where an output of a probability of a potential source of error is provided is shown. As with the method depicted in FIG. 8, it may be initially desirable to determine whether a patient's symptoms are indicative of inappropriate dosing (510). If the symptoms are indicative of an under-dose, overdose, or the like, a determination may be made as to the probability that a particular source or error may contribute to the inappropriate dosing. In the depicted embodiment, a determination is made as to the probability that programming error contributes, or has contributed, to inappropriate dosing (900). Of course such determinations may also be made with regard to other potential sources described or contemplated herein. The probability that the potential source (in the depicted embodiment, programming error) contributes, or has contributed, to inappropriate dosing may then be output (910).

As used herein, "programming error" in the context of programming an infusion device to deliver a therapeutic agent to a particular patient, means that the programmed parameters with regard to the particular patient are inappropriate. It does not necessarily mean a healthcare provider accidentally entered programming instructions that they did not intend to enter (which may also be the case).

In many embodiments, determinations as to whether a source of inappropriate dosing exists or the probability that a potential source contributes, or has contributed, to inappropriate dosing may include comparing data regarding the potential source to a lookup table. In some embodiments, determinations as to whether a source of inappropriate dosing exists or the probability that a potential source contributes, or has contributed, to inappropriate dosing may consist of, or consist essentially of, comparing data regarding the potential source to a lookup table.

By way of example, data regarding infusion rate of a drug may be compared to a lookup table to determine the likelihood of underdosing or overdosing. For purposes of example, the lookup table may include information as shown in Table 1 below.

TABLE 1

Examples of data in lookup table regarding appropriate dosing

| Therapeutic Agent | Conc. | Daily Dose | Likelihood of Overdose Symptom | Likelihood of Underdose Symptom |
|---|---|---|---|---|
| Therapeutic agent A | 10 mg/ml | 0.1-.02 mg | 0% | 95% |
| | | 0.2-1 mg | 10% | 75% |
| | | 1-2 mg | 25% | 50% |
| | | 2-5 mg | 50% | 25% |
| | | 5-10 mg | 75% | 10% |
| | | 10-20 mg | 95% | 0% |
| Therapeutic agent B | 5 mg/ml | 0.1-.02 µg | 0% | 95% |
| | | 0.2-1 µg | 10% | 75% |
| | | 1-2 µg | 25% | 50% |
| | | 2-5 µg | 50% | 25% |
| | | 5-10 µg | 75% | 10% |
| | | 10-20 µg | 95% | 0% |

It will be understood that the dosing and probabilities that such dosing may contribute to underdosing or overdosing presented in Table 1 are for purposes of illustration only. Appropriate dosing ranges and probabilities of such dosing ranges contributing to overdosing or underdosing may be based on empirical evidence collected by healthcare providers or device manufacturers over time. The data in the lookup tables may be updated or refined as more information is collected with regard to whether patients present with overdose or underdose symptoms when receiving particular doses of therapeutic agent. It may be desirable to collect data from a variety of healthcare providers on a large population of patients to populate the lookup table. While not shown, it will be understood that the device used, the target location of drug delivery, etc. may affect the likelihood that a particular dose may contribute to an inappropriate dosing system, and such information may be included in the lookup table.

If the infusion device parameters appear to be within ranges that would not typically lead to underdosing or overdosing symptoms, device and catheter performance may be evaluated. For example, if the device has been determined to have failed, the source of the failure may be evaluated and the probability that the failure contributes to underdosing or overdosing may be determined. Again, such a determination may comprise, consist essentially of, or consist of comparing data regarding device status to a lookup table. By way of example, if a battery is depleted or became depleted for some time, as may happen with a rechargeable battery, or if a pumping mechanism failure has occurred, the likelihood of an underdose being due to the device failure may be high, while the likelihood that the failure contributes to an overdose is low.

By way of further example, data regarding catheter status may be compared to a lookup table to determine, or as a part of determining, whether catheter performance or a catheter complication contributes to underdose or overdose symptoms. This determination may comprise, consist essentially of, or consist of comparing catheter status data to a lookup table. For example, if the catheter is occluded, underdosing may be likely. The degree of occulusion may affect the likelihood of underdosing. If the catheter is dislodged from the infusion device, causing the therapeutic agent to be delivered to a different area of the body (in proximity to the infusion device) than the target location (distal end of the catheter), the likelihood that underdosing symptoms will be observed may increase. In some cases, a dislodgement may result in an increase in side effects. For example, if a drug is toxic when delivered systemically, but not when delivered centrally, then dislodgement of, for example, an intrathecal catheter may result increased likelihood of side effects. A tear or leak in a catheter may have similar effects, as may migration of the distal portion of the catheter from the target location.

Any suitable method may be used to determine the status of the catheter (e.g., occluded, torn, dislodged, migrated, etc.). For example, one or more pressure sensors and appropriate electronics and software may be employed to determine catheter status. Examples of pressure sensing to determine catheter status are described in, for example, commonly assigned patents and published patent applications such as: US 2008/0009837, US 2010/0069841, US 2008/0243074, US 2010/0168607 US 2007/0270782, U.S. Pat. No. 7,320,676, US 2008/0097287, and US 2010/0010646, which patents and published patent applications are hereby incorporated herein by reference in their entireties to the extent that they do not conflict with the present disclosure.

Other methods include injection of dye through the catheter (e.g., via reservoir or catheter access port), performing x-rays of the device, and aspirating via a catheter access port to determine the status of the catheter. With these other methods, a user may enter observations regarding the results, e.g. "occlusion", "tear", "dislodgement", "migration", "normal". In some embodiments, a list of choices is presented to the user to select for inputting catheter status. In cases where pressure sensing testing is performed, data collected from the infusion device may be transmitted to an external device as input.

Figure 10:
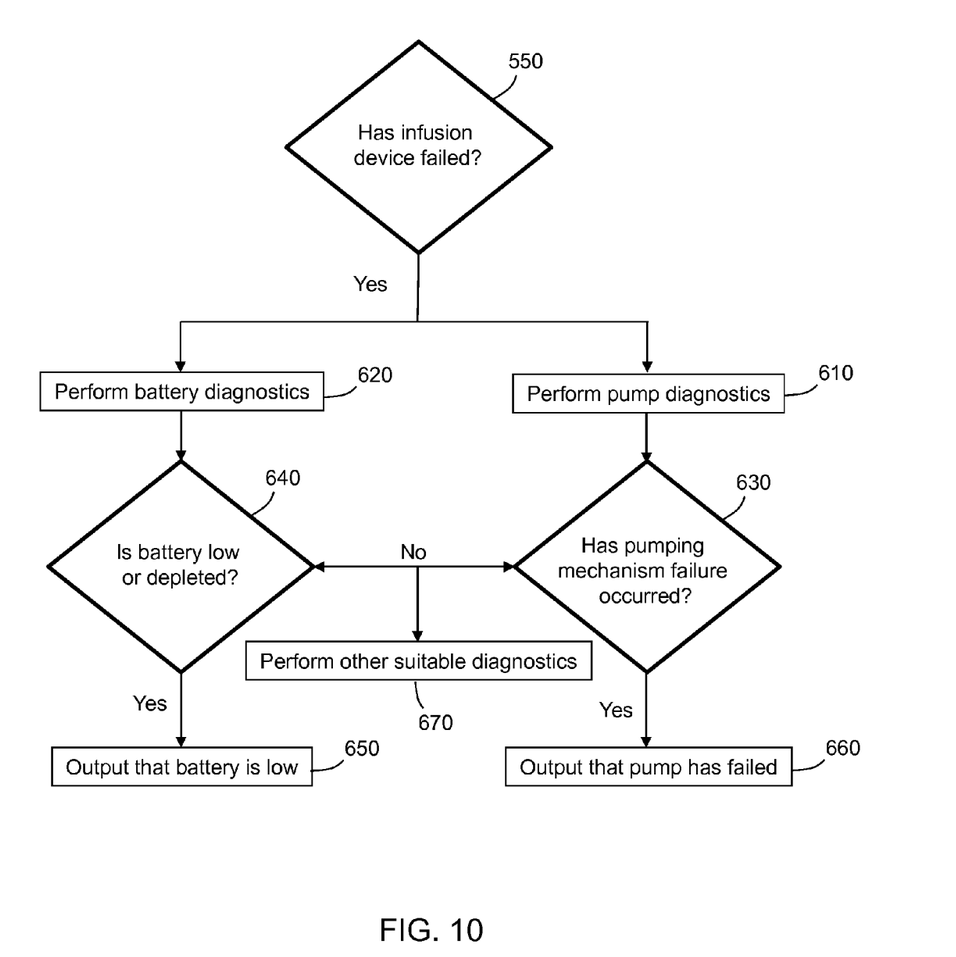

Referring now to FIG. 10, an example of steps that may be taken if an infusion device failure has occurred or is suspected to have occurred (550) is shown. If a device failure is determined or suspected, a variety of device diagnostics may be performed. Typically infusion devices, particularly programmable infusion devices, are configured to perform such diagnostics and transmit the results wirelessly to external devices. In the brief example depicted in FIG. 10, battery diagnostics (620) or pump diagnostics (610) may be performed. E.g., the infusion device may test the battery or pump or may review past battery or pump performance data that has been stored in memory. If the battery is determined to be depleted or have been depleted (640) appropriate output may be displayed (650), for example on a display of an external device as depicted in FIG. 1. If a pumping mechanism failure has occurred, or is determined to have previously occurred (630), appropriate output regarding the pump failure may be displayed (660). Of course, other suitable pump or catheter diagnostics may be performed (670) and the results of such diagnostic tests may be displayed or otherwise presented.

Figure 11:
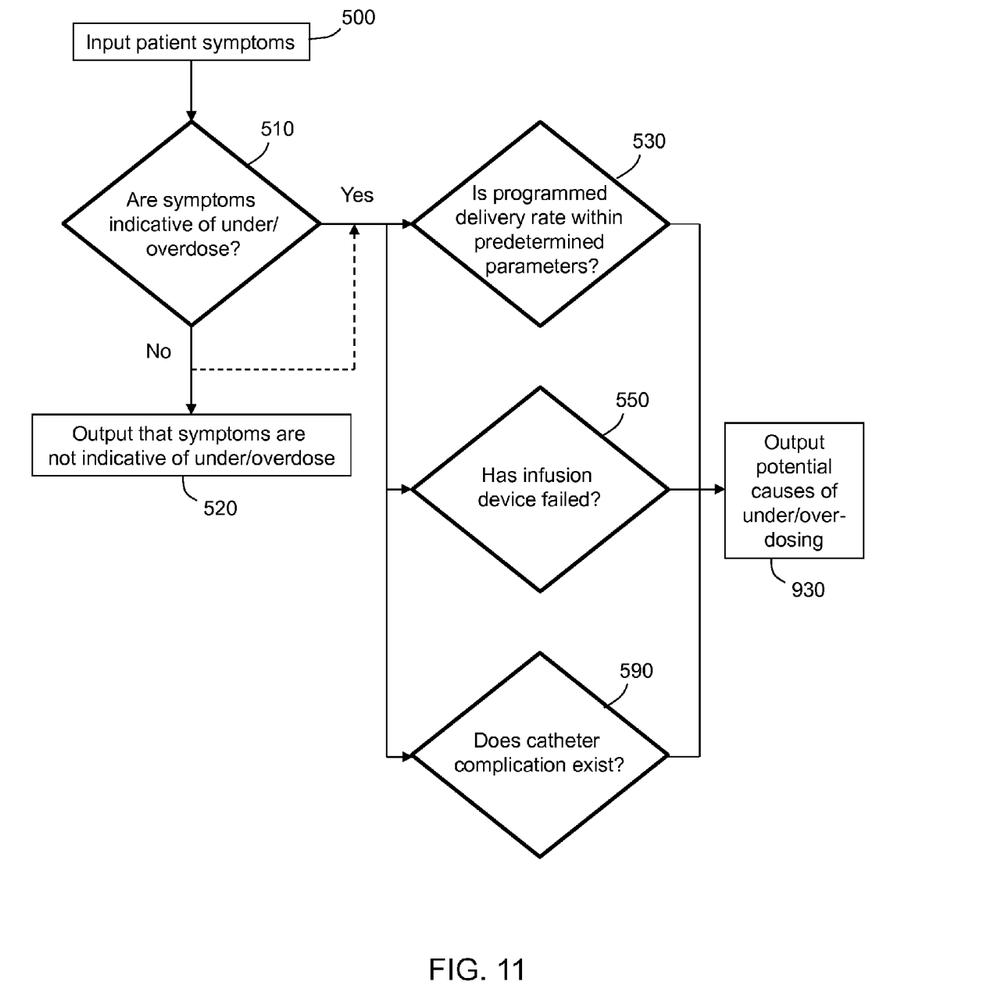

Referring now to FIG. 11, a method similar to that of FIG. 8 is depicted, with like reference numbers to referring to the same or similar steps. As shown in FIG. 11, device and catheter performance determinations (530, 550, 590) may occur simultaneously or regardless of the outcome of other device or catheter performance determinations. That is, if the patient's symptoms are indicative of underdosing or overdosing, a predetermined set of pump or catheter performance diagnostics may be automatically run. Based on the information of all of the diagnostics, an output may be presented as to the potential source of inappropriate dosing (930). As discussed above, with regard to FIGS. 8-9, the probability that a particular potential source contributes to the inappropriate dosing may also be output.

Figure 12:
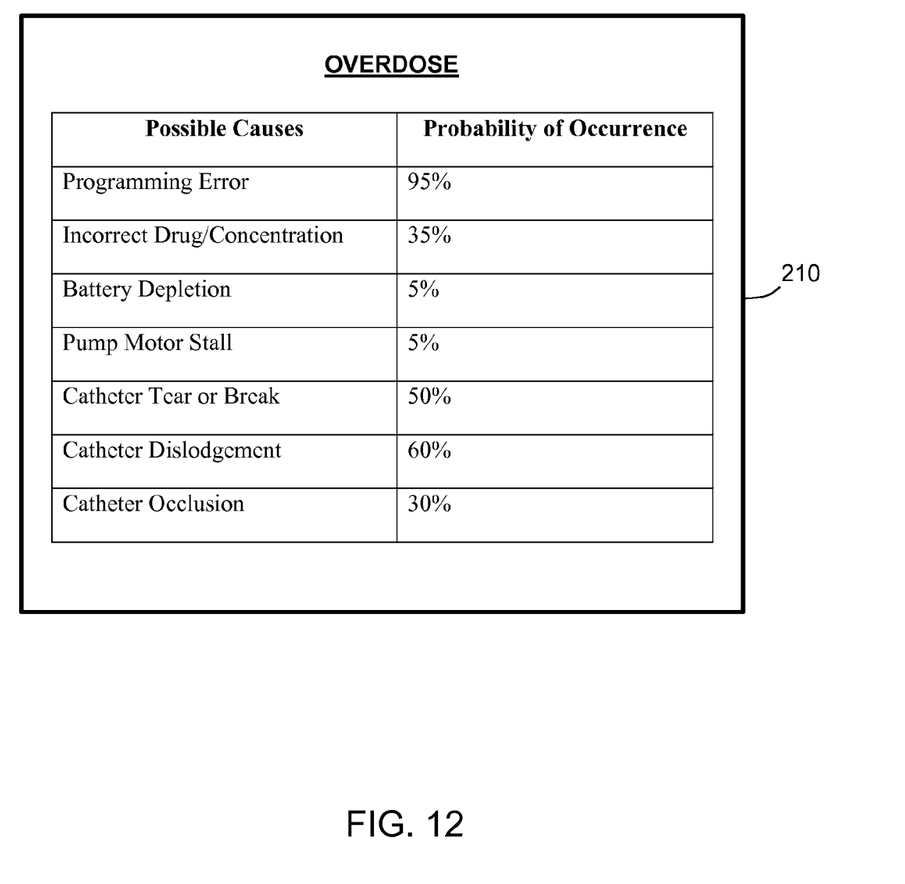
FIGS. 12-14 are schematic screenshots of examples of displays that may be presented in accordance with embodiments described herein.

Regardless of whether pump and catheter diagnostics, and associated determinations, are made sequentially, simultaneously or automatically, the output may appear similar. An example of an output that may be displayed in shown in FIG. 12. The output may be presented on a display 210 (e.g., of device 200 as depicted and described above). As shown in FIG. 12, the determination as to whether inappropriate dosing is likely to have occurred is displayed ("OVERDOSE" in this case), as well as possible causes and the probability that the possible causes contribute to the inappropriate dosing.

Once an inappropriate dosing situation has been determined to occur, a user may be prompted to take certain actions relevant to the nature of the inappropriate dosing. For example and with reference to FIGS. 13-14, examples of displays prompting a user to take action are presented. The information may be presented on display 210 (e.g., of device 200 as depicted and described above). The information depicted in FIGS. 13-14 is an example of what may be presented in an overdose situation.

Figure 13:
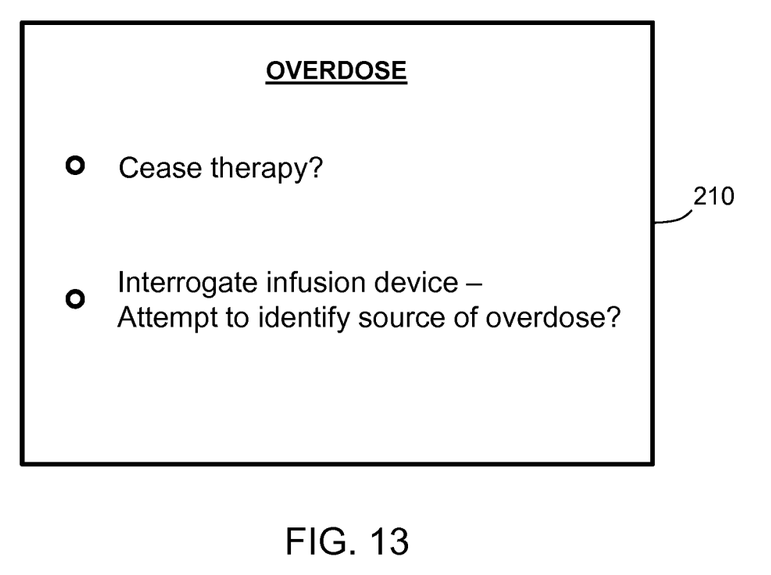

For example, with reference to FIG. 13, a user may be asked whether to cease therapy (i.e., stop delivery of therapeutic agent from implanted infusion device). Should the user choose to stop therapy, appropriate instructions may be transmitted to the implanted infusion device (e.g., via external device 200 as depicted and described above). As further shown in FIG. 13 by way of example, the user may be asked to interrogate the infusion device to identify potential sources of inappropriate dosing. In some embodiments, such interrogation will be performed automatically without prompting a user.

Figure 14:
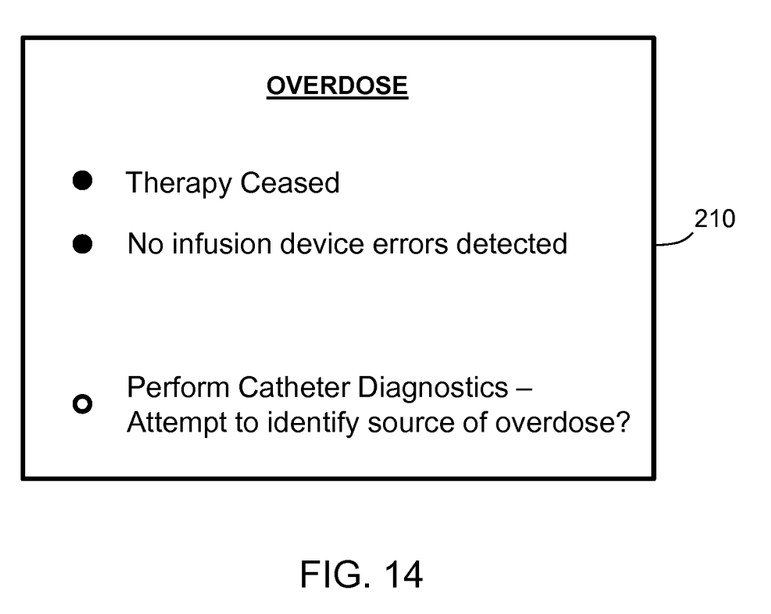

With reference to FIG. 14, the display 210 indicates to user that the therapy has been stopped and that no infusion device errors have been detected and prompts the user as to whether catheter diagnostics should be performed. In some embodiment, such diagnostics will be performed automatically. In cases where the catheter diagnostics are done manually (e.g., use of a dye, x-ray or aspiration), step by step instructions for performing such diagnostics (not shown) may be presented on the display 210. It will be understood that in some cases automatic stopping of therapy may not be advisable due to patient safety concerns (e.g., abrupt withdrawal symptoms may result).

Thus, systems, devices and methods for EVALUATING DOSING FROM AN

IMPLANTABLE INFUSION DEVICE are described. Those skilled in the art will recognize that the preferred embodiments described herein may be altered or amended without departing from the true spirit and scope of the disclosure, as defined in the accompanying claims.

What is claimed is:

1. A method for gauging the performance of an infusion system implanted in a patient, the method comprising:
receiving input into an external device regarding the identity of a therapeutic agent contained in an implanted infusion device of the infusion system, the external device being capable of communicating with an implanted infusion device of the infusion system;
displaying on the external device a predetermined set of symptoms associated with the therapeutic agent;
receiving input into the external device regarding with which of the predetermined set of symptoms the patient presents;
determining whether the therapeutic agent is being delivered, or has been delivered, at an appropriate dose to the patient based on the input identity of the therapeutic agent and the patient's presented symptoms;
displaying on the external device whether the patient is receiving the appropriate dose of the therapeutic agent;
interrogating the infusion device to identify at least one potential source of inappropriate dosing if it is determined that the therapeutic agent is not being delivered, or has not been delivered, at an appropriate dose;
displaying on the external device the at least one potential source of the inappropriate dosing based on the interrogation of the implanted infusion device; and
determining probabilities that the at least one potential source contributes to the inappropriate dosing by comparing data regarding the at least one potential source to a lookup table and displaying the probabilities for the displayed at least one potential source.

2. The method of claim 1, wherein receiving input regarding the identity of the therapeutic agent comprises receiving the input from the implanted infusion device.

3. The method of claim 2, further comprising interrogating the implanted infusion device regarding the identity of the therapeutic agent.

4. The method of claim 1, wherein determining whether the therapeutic agent is being delivered, or has been delivered, at an appropriate dose to the patient comprises comparing the patient's symptoms to a lookup table comprising data regarding the predetermined set of symptoms associated with the therapeutic agent.

5. The method of claim 4, wherein the lookup table resides on a database remote from the external device and wherein the database compiles symptom information from other patients receiving the same therapeutic agent at a same target location of delivery via other implanted infusion devices device.

6. The method of claim 1, wherein the displayed at least one potential source include one or more of (i) programming error; (ii) incorrect therapeutic agent; (iii) incorrect concentration of therapeutic agent; (iv) battery depletion; (v) pumping mechanism failure; (vi) catheter tear or break; (vii) catheter occlusion; (viii) catheter migration; and (ix) catheter dislodgement.

7. The method of claim 6, further comprising determining probabilities that the at least one potential source contributes to the inappropriate dosing by comparing data regarding the at least one potential source to a lookup table and displaying the probabilities for each of the displayed at least one potential source.

8. The method of claim 1, further comprising displaying potential diagnostic interventions for the displayed at least one potential source.

9. The method of claim 8, further comprising prompting a user to select a diagnostic intervention.

10. The method of claim 1, wherein the infusion system comprises a catheter operably coupled to the implanted infusion device for delivering the therapeutic agent to a predetermined location of the patient, the method further comprising instructing the implanted infusion device to perform a catheter complication test.

11. The method of claim 10, further comprising displaying at least one potential catheter complication that includes one or more of catheter break or tear, catheter migration, catheter dislodgement, and catheter occlusion that may exist and displaying a probability of exisentence for the displayed at least one catheter complication.

12. A method for identifying at least one potential source of inappropriate dosing of a therapeutic agent from an implantable infusion system, the infusion system comprising an implanted infusion device having a reservoir for containing the therapeutic agent and a catheter operably coupled to the reservoir for delivering the therapeutic agent to a predetermined location of the patient, the method comprising:
- receiving input regarding the identity of the therapeutic agent into an external device, the external device being capable of communicating with the implanted infusion device;
- displaying on the external device a predetermined set of symptoms associated with the therapeutic agent;
- receiving input into the external device regarding with which of the predetermined set of symptoms the patient presents;
- determining whether the therapeutic agent is being delivered, or has been delivered, at an appropriate dose to the patient based on the input identity of the therapeutic agent and the patient's presented symptoms;
- displaying on the external device whether the patient is receiving the appropriate dose of the therapeutic agent;
- interrogating the implanted infusion device to identify at least one potential source of inappropriate dosing if it is determined that the therapeutic agent is not being delivered, or has not been delivered, at an appropriate dose;
- instructing the infusion device to perform a catheter complication test if a catheter complication is identified as a potential source of the inappropriate dosing;
- displaying on the external device the at least one potential source of the inappropriate dosing based on the input identity of the therapeutic agent, the patient's presented symptoms, the interrogation of the implanted infusion device, if performed, and the catheter complication test, if performed; and
- calculating probabilities that the at least one potential source contributes to the inappropriate dosing by comparing data regarding the at least one potential source to a lookup table and displaying the probabilities probability for the displayed at least one potential source.

13. The method of claim 12, wherein the displayed at least one potential source includes sources include one or more of (i) programming error; (ii) incorrect therapeutic agent; (iii) incorrect concentration of therapeutic agent; (iv) battery depletion; (v) pump motor stall; (vi) catheter tear or break; (vii) catheter dislodgement; (viii) catheter migration; and (ix) catheter dislodgement.

* * * * *